United States Patent [19]

Kershner

[11] Patent Number: 5,242,878
[45] Date of Patent: Sep. 7, 1993

[54] CATALYST FOR SYNTHESIS OF A POLYKETONE

[75] Inventor: David L. Kershner, Bronxville, N.Y.

[73] Assignee: Akzo N.V., Arnhem, Netherlands

[21] Appl. No.: 865,413

[22] Filed: Apr. 8, 1992

[51] Int. Cl.$^5$ .............................................. B01J 31/00
[52] U.S. Cl. ................................... 502/166; 502/162; 502/169
[58] Field of Search ..................... 502/162, 166, 169

[56] References Cited

U.S. PATENT DOCUMENTS

| | | | |
|---|---|---|---|
| 4,740,625 | 4/1988 | Drent | 528/392 |
| 4,818,810 | 4/1989 | Drent | 528/392 |
| 5,057,599 | 10/1991 | Wong | 502/162 |

FOREIGN PATENT DOCUMENTS 408155 1/1991 European Pat. Off. .

*Primary Examiner*—Patrick P. Garvin
*Assistant Examiner*—Brent M. Peebles
*Attorney, Agent, or Firm*—Richard P. Fennelly; Louis A. Morris

[57] ABSTRACT

Polyketones can be formed from carbon monoxide and at least one olefin by using, as a catalytic complex, a catalyst which comprises a Group VIII metal, an anion of an acid having a pK$_a$ of less than about four, and a tin tetradentate phosphine ligand, preferably of the formula Sn(RPR'$_2$)$_4$ where R is methylene and R' is phenyl.

4 Claims, No Drawings

CATALYST FOR SYNTHESIS OF A POLYKETONE

BACKGROUND OF THE INVENTION

It is well known that a polyketone can be synthesized by the polymerization of carbon monoxide and at least one olefin. A variety of catalyst formulations have been described for such a polymerization procedure.

One representative type of catalyst system, which is described in U.S. Pat No. 4,818,810, is formed by the admixture of a Group VIII metal, such as palladium, cobalt or nickel, an anion of an acid having a very low $pK_a$, e.g. lower than about two, and a bidentate ligand which comprises phosphorus, arsenic or antimony A more recent patent publication which shows the use of tetrakisphosphine ligands is European Patent Publication No. 408,155 which describes catalyst compositions comprising a Group VIII metal and a tetrakisphosphine of the general formula $(R^1R^2P)_4R^5$ where $R^1$ and $R^2$ are hydrocarbyl groups and $R^5$ represents a tetravalent organic group which connects the four phosphorus atoms and which has a structure of at least two carbon atoms between every phosphorus atom. The catalyst systems described in this patent publication are also said to advantageously include an anion of an acid having a $pK_a$ of less than about four.

SUMMARY OF THE PRESENT INVENTION

The present invention is a catalyst for the formation of a polyketone from carbon monoxide and at least one olefin which comprises, as a catalytic complex, a Group VIII, an anion of an acid having a $pK_a$ of less than about four and a tin tetradentate phosphine ligand. The tin tetradentate phosphine ligand of the present invention is deemed to be a novel component of the aforementioned type of catalyst and it preferably is of the formula $Sn(RPR'_2)_4$ where R is methylene and R' is preferably phenyl.

DETAILED DESCRIPTION OF THE INVENTION

The foregoing catalyst system contains certain elements which are known and conventional in the art of forming catalyst complexes for the synthesis of polyketones. Included within these known components is the Group VIII metal and the anion of an acid having a $pK_a$ of less than about four.

Representative Group VIII metals which can be used in the catalyst of the present invention include the metals palladium, nickel and cobalt, with palladium being the most preferred. Suitable sources for such metals include the salts of such metals with acids such as nitric, sulfuric or alkanoic acids containing no more than about twelve carbon atoms. The most preferred compound for use in forming the present catalyst is palladium acetate. The anion of the acid having a $pK_a$ of less than about four include such mineral acids as sulfuric and perchloric acid, sulfonic acids, such as para-toluenesulfonic acids and halocarboxylic acids such as trichloroacetic acid, difluoroacetic acid and trifluoroacetic acid. Para-toluenesulfonic acid is the preferred acid for use in the present invention.

The novel component in the catalyst of the present invention is a tin tetradentate phosphine ligand such as one having the formula $Sn(RPR'_2)_4$, where R is a methylene moiety and R' is phenyl.

The catalyst of the present invention can be formed rather easily be dissolving the Group VIII metal salt, the tin tetradentate phosphine ligand, and the selected acid in a suitable solvent such as acetone at room temperature. Preferably the molar amounts of Group VIII metal salt and tin-containing ligand are substantially equimolar with the amount of acid being present in molar excess. Volatiles from the reaction can be removed and, if necessary, any solid product forming from the reaction can be dissolved in a higher amount of solvent if necessary. The catalyst complex can be used in solution to polymerize the polyketone.

The present invention is further illustrated by the Examples which follow.

EXAMPLE 1

A complex prepared from tetramethylenediamine (TMEDA) and diphenylphosphinomethyl lithium, $LiCH_2PPh_2$, (5.00 g; 15.5 mmol), Inorg. Chem. 1981, 20, 3200, was dissolved in 100 ml of tetrahydrofuran, and $SnCl_4$ (0.89 g; 0.40 ml; 3.4 mmol) was added to the tetrahydrofuran solution at room temperature. The resultant solution was stirred at room temperature for eighteen hours. The solution was then refluxed for three hours. The solution was then reduced to an oily resin under vacuum, and the resin was treated with toluene (50 ml). Excess anhydrous $NH_4Cl$ was added to the mixture, and the mixture was filtered. Addition of hexane to the filtrate yielded the product, tetrakis(diphenylphosphino methyl) stannane, $(Sn(CH_2PPh_2)_4$ as a white solid. Yield: 1.8 g; 2.0 mmol; 58%. Melting point: 151°-153° C. $^{31}P$ NMR ($CDCl_3$; 85% $H_3PO_4$ external reference): −9.0 ppm.

EXAMPLE 2

A catalyst was prepared by dissolving palladium acetate (0.045 g; 0.20 mmol), $Sn(CH_2PPh_2)_4$ (0.19 g; 0.21 mmol), and para-toluenesulfonic acid (0.106 g; 0.56 mmol) in 20 ml of acetone at room temperature. The volatiles were then removed under reduced pressure to yield an orange colored resin. The resin was dissolved in 500 ml of acetone, and the solution was charged to a 1 liter autoclave. The reactor was charged to a pressure 1000 psi with a 1:1 CO:ethylene gas mixture, and the contents of the autoclave were heated to 65° C. A constant pressure of 1000 psi of CO:ethylene was maintained during the polymerization. After eighteen hours the reactor was cooled and vented. The polymer was collected and air-dried dried. The yield of polymer was 2.1 g which corresponds to an activity of 66 g polymer/g Pd.

EXAMPLE 3

A polymerization was performed in a manner similar to that described in Example 2 except the catalyst was prepared from palladium acetate (0.056 g; 0.25 mmol), $Sn(CH_2PPh_2)_4$ (0.11 g; 0.12 mmol), and para-toluenesulfonic acid (0.10 g; 0.52 mmol). The yield of polymer was 39.0 g, which corresponds to an activity of 1470 g polymer/g Pd.

EXAMPLE 4

A polymerization was performed in a manner similar to that described in Example 2 except the catalyst was prepared from palladium acetate (0.056 g; 0.25 mmol), $Sn(CH_2PPh_2)_4$ (0.11 g; 0.12 mmol) and trifluoroacetic acid (0.04 ml; 0.52 mmol). The yield of polymer was 24.0, which corresponds to an activity of 906 g polymer/g Pd.

EXAMPLE 5

A catalyst containing palladium acetate (0.22 g; 1.0 mmol), $Sn(CH_2PPh_2)_4$ (0.46 g; 0.5 mmol) and para-toluenesulfonic acid (0.42 g; 2.2 mmol) was prepared in a manner similar to that described in Example 2. The resultant orange-colored resin was redissolved in 4 liter of acetone, and the acetone solution was charged to a 10 liter stainless steel autoclave. Propylene (1.5 liter) was charged to the autoclave, and a 1:1 (vol/vol) CO/ethylene gas mixture was charged to the autoclave until a pressure of 730 PSIG was attained. The polymerization was allowed to proceed at 30° C. and at a constant pressure of 730 PSI of CO/ethylene for 60 hr. The autoclave was then cooled and vented. The resultant solid was collected and air dried. The yield of polymer was 172 g which corresponds to an activity of 1600 g polymer/g Pd. Melting point (dec.) of polymer: 232° C.

EXAMPLE 6

A catalyst was prepared in a manner analogous to that described in Example 5. The resultant acetone solution (4 liter) was charged to a 10 liter stainless steel autoclave. Propylene (1.5 liter) was added to the autoclave, and CO was charged to the autoclave until a pressure of 750 PSIG was attained. The polymerization was allowed to proceed at 30° C. and at a constant pressure of 750 PSI of CO for 60 hr. The autoclave was then vented, and the solution was evaporated under a stream of $N_2$ to yield a yellow resin. The yield of polymer was 56 g which corresponds to an activity of 530 g polymer/g Pd.

The foregoing Examples are presented for illustrative purposes only and should not be construed in a limiting sense for this reason. The scope of protection that is sought is set forth in the claims which follow.

We claim:

1. A catalyst complex for the formation of a polyketone from carbon monoxide and at least one olefin which is formed from : (a) a Group VIII metal salt; (b) an anion of an acid having a $pK_a$ of less than about 4; and (c) a tin tetradentate phosphine ligand of the formula $Sn(RPR'_2)_4$, where R is methylene and R' is phenyl.

2. A catalyst as claimed in claim 1 wherein the Group VIII metal is palladium.

3. A catalyst as claimed in claim 1 wherein the anion is derived from para-toluenesulfonic acid.

4. A catalyst as claimed in claim 1 wherein the Group VIII metal is palladium and the anion of the acid is derived from para-toluenesulfonic acid.

* * * * *